(12) United States Patent
Bergeron, Jr.

(10) Patent No.: US 6,342,534 B1
(45) Date of Patent: *Jan. 29, 2002

(54) ANALOGS OF BIOLOGICALLY ACTIVE, NATURALLY OCCURRING POLYAMINES, PHARMACEUTICAL COMPOSITIONS AND METHODS OF TREATMENT

(75) Inventor: Raymond J. Bergeron, Jr., Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/688,386

(22) Filed: Oct. 17, 2000

Related U.S. Application Data

(63) Continuation of application No. 08/080,642, filed on Jun. 22, 1993, now Pat. No. 6,184,232, which is a continuation-in-part of application No. 07/834,345, filed on Feb. 12, 1992, now Pat. No. 5,342,945, which is a division of application No. 07/210,520, filed on Jun. 23, 1988, now Pat. No. 5,091,576, which is a continuation-in-part of application No. 07/066,227, filed on Jun. 25, 1987, now abandoned, which is a continuation-in-part of application No. 06/936,835, filed on Dec. 2, 1986, now abandoned.

(51) Int. Cl.$^7$ .................... A61K 31/13; A61K 31/445; C07C 211/00; C07D 211/00
(52) U.S. Cl. ................ 514/673; 514/674; 514/316; 564/511; 564/512; 546/186
(58) Field of Search ................ 514/673, 674, 514/316; 564/512, 511; 546/186

(56) References Cited

U.S. PATENT DOCUMENTS

| | | | |
|---|---|---|---|
| 4,104,248 A | 8/1978 | Cantor | |
| 4,153,567 A | 5/1979 | Kluzer et al. | |
| 4,321,354 A | 3/1982 | Kluzer et al. | |
| 4,505,928 A | 3/1985 | Amundson et al. | |
| 4,591,065 A | 5/1986 | Ray | |
| 4,783,482 A | 11/1988 | Amundson et al. | |
| 4,977,177 A | 12/1990 | Bommer et al. | |
| 5,091,576 A | 2/1992 | Bergeron | |
| 5,109,024 A | 4/1992 | Prakash et al. | |
| 5,124,339 A | 6/1992 | King | |
| 5,128,353 A | 7/1992 | Bergeron | |
| 5,173,505 A | 12/1992 | Bergeron | |
| 5,432,202 A | * 7/1995 | Cherksey et al. | 514/626 |
| 5,541,230 A | * 7/1996 | Basu et al. | 514/642 |
| 5,627,215 A | * 5/1997 | Frei et al. | 514/674 |
| 5,654,484 A | * 8/1997 | Prakash et al. | 564/511 |
| 5,874,627 A | * 2/1999 | Angell et al. | 564/512 |
| 5,902,897 A | * 5/1999 | Wamprecht et al. | 560/159 |
| 5,929,283 A | * 7/1999 | Uno et al. | 564/506 |
| 6,127,384 A | * 10/2000 | Dianna et al. | 514/316 |
| 6,184,232 B1 | * 2/2001 | Bergeron, Jr. | 514/316 |

FOREIGN PATENT DOCUMENTS

| | | |
|---|---|---|
| JP | 52 118 405 | 10/1997 |

OTHER PUBLICATIONS

Janne et al., A. Biochim. Biophys. Acta., vol. 473, pp 241, (1978).
Fillingname et al., Proc. Natl. Acad. Sci. U.S.A., vol. 72, p. 4042 (1975).
Metcalf et al., J. Am. Chem. Soc., vol. 100, p. 2551 (1978).
Flink et al., Nature, (London), vol. 253, p. 62, (1975).
Pegg et al., Polyamine Metabolism and Function, Am. J. Cell. Physiol., vol. 243, pp. 212–221 (1982).
Dkystra et al., Science, vol. 149, p. 48 (1965).
Russell et al., Polyamines as Biochemical Markers of Normal and Malignant Growth (Raven, New York, 1978).
Hirschfield et al., J. Bacteriol., vol. 101, p. 725 (1970).
Hafner et al., J. Biol. Chem., vol. 254, p. 12419 (1979).
Cohn et al., J. Bacteriol., vol. 134, p. 208 (1978).

(List continued on next page.)

Primary Examiner—Deborah C. Lambkin
(74) Attorney, Agent, or Firm—Miles & Stockbridge; Dennis P. Clark

(57) ABSTRACT

Polyamines having the formula:

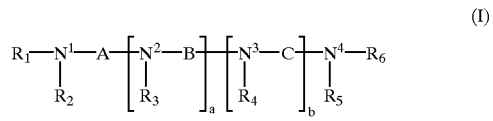

(I)

or a salt thereof with a pharmaceutically acceptable acid wherein:

$R_1$–$R_6$ may be the same or different and are alkyl, aryl, aryl alkyl, cycloalkyl, optionally having an alkyl chain interrupted by at least one etheric oxygen atom, or hydrogen;

$N^1$, $N^2$, $N^3$ and $N^4$ are nitrogen atoms capable of protonation at physiological pH's;

a and b may be the same or different and are integers from 1 to 4;

A, B and C may be the same or different and are bridging groups which effectively maintain the distance between the nitrogen atoms such that the polyamines:
  (i) are capable of uptake by a target cell upon administration thereof to a human or non-human animal; and
  (ii) upon uptake by the target cell, competitively bind via an electrostatic interaction between the positively charged nitrogen atoms to substantially the same biological counter-anions as the intracellular natural polyamines in the target cell;

the polyamines, upon binding to the biological counter-anion in the cell, function in a manner biologically different than the intracellular polyamines, the polyamines not occurring in nature; as well as pharmaceutical compositions embodying the polyamines and methods of treating patients requiring anti-neoplastic therapy.

8 Claims, 8 Drawing Sheets

OTHER PUBLICATIONS

Pohjatipelto et al., *Nature* (London), vol. 293, p. 475 (1981).

Mamont et al., *Biochem. Biophys. Res. Commun.*, vol. 81, p. 58, (1978).

Bloomfield et al., *Polyamines in Biology and Medicine* (D.R. Morris and L.J. Morton, eds., Dekker, New York, 1981) pp. 183–205.

Gosule et al., *Nature*, vol. 259, p. 333, (1976).

Gabbay et al., *Ann. N.Y. Acad. Sci.*, vol. 171, p. 810, (1970).

Suwalsky et al., *J. Mol Biol.*, vol. 42, p. 363 (1969).

Liquori et al., *J. Mol. Biol.*, vol. 24, p. 113 (1968).

Sjoerdsma et al., *Butterworths Int. Med. Rev.: Clin. Pharmacol. Thera.*, vol. 35, p. 287 (1984).

Israel et al., *J. Med. Chem.*, vol. 16, p. 1 (1973).

Morris et al., *Polyamines in Biology and Medicine*, Dekker, New York, p. 223 (1981).

Wang et al., *Biochem. Biophys. Res. Commun.*, vol. 94, p. 85 (1980).

*Cancer Res.*, vol. 49, "The role of methylene backbone in the anti–proliferative activity of polyamine analogues on L1210 cells," Bergeron et al., pp. 2959–2964 (1989).

*J. Med. Chem.*, vol. 31, "Synthetic polyamine analogues as analogues as antineoplastics," Bergeron et al., pp. 1183–1190 (1988).

*Polyamines in Bio–chemical and Clinical Research*, "Regulation of polyamine biosynthetic activity by spermidine and spermine–a novel antiproliferative strategy," Porter et al., pp. 667–690 (1988).

*Cancer Res.*, vol. 49, "Major increases in spermidine/spermine–$N^1$–acetyl transferase activity by spermine analogues and their relationship to polyamine depletion and growth inhibition in L1210 cells," Basu et al., pp. 6226–6231 (1989).

*Biochem. J.*, vol. 267, "Induction of spermidine/spermine $N^1$–acetyltransferase activity in Chinese–hamster ovary cells by $N^1,N^{11}$–bis(ethyl)nonspermine and related compounds," Pegg et al, pp. 331–338 (1990).

Biochem. J., vol. 268, "Combined regulation of ornithine and S–adenosylmethionine decarboxylases by spermine and the spermine analogue $N^1N^{12}$–bis–(ethyl)spermine," Porter et al., pp. 207–212 (1990).

*Cancer Res.*, vol. 50, "Effect of $N^1,N^{14}$–bis(ethyl)–homospermine on the growth of U–87 MG and SF–126 on human brain tumor cells," Basu et al., pp. 3137–3140 (1990).

*Biochem. Biophys. Res. Commun.*, vol. 152, "The effect of structural changes in a polyamine backbone on its DNA binding properties," Stewart, pp. 1441–1446 (1988).

*J. Org. Chem.*, vol. 45, "Synthesis of $N^4$–acylated $N^1,N^8$–bis(acyl) spermidines: An approach to the synthesis of siderophores," Bergeron et al., pp. 1589–1592 (1980).

*Synthesis*, "Reagents for the selective acylation of spermidine, homospermidine and bis–[3–amino–propyl]amine," Bergeron et al., pp. 732–733 (1981).

*Synthesis*, "Reagents for the selective secondary functionaliza–tion of linear triamines," Bergeron et al., pp. 689–692 (1982).

*Synthesis*, "Amines and polyamines from nitriles," Bergeron et al., pp. 782–785 (1984).

*J. Org. Chem.*, vol. 49, "Reagents for the stepwise functional–ization of spermidine, homospermidine and bis–[3–aminopropyl] amine," Bergeron et al., p. 2997 (1984).

*Accts. Chem. Res.*, vol. 19, "Methods for the selective modifi–cation of spermidine and its homologues," Bergeron, pp. 105–113 (1986).

*Bioorg. Chem.*, vol. 14, "Hexahydropyrimidines as masked spermi–dine vectors in drug delivery," Bergeron et al., pp. 345–355 (1986).

*J. Org. Chem.*, vol. 53, "Reagents for the stepwise functionali–zation of spermine," Bergeron et al., pp. 3108–3111 (1988).

*J. Org. Chem.*, vol. 52, "Total synthesis of (±)–15–Deoxyspergualin," Bergeron et al., pp. 1700–1703 (1987).

*J. Org. Chem.*, vol. 56, "The total synthesis of Alcaligin," Bergeron et al., pp. 586–593 (1991).

*CRC Handbook on Microbial Iron Chelates*, "Synthesis of catecho–lamide and hydroxamate siderophores," Bergeron et al., pp. 271–307 (1991).

*Cancer Res.*, vol. 46, "A comparison and characterization of growth inhibition by alpha–Difluoromethylornithine (DFMO), and inhibitor of ornithine decarboxylase and $N^1,N^8$–bis(ethyl)spermi–dine (BES), an apparent regulator of the enzyme," Porter et al., pp. 6279–6285 (1986).

*Cancer Res.*, vol. 47, "Relative abilities of bis(ethyl) deriva–tives of putrescine, spermidine and spermine to regulate poly–amine biosynthesis and inhibit L1210 leukemia cell growth," Porter et al., pp. 2821–2825 (1987).

*Cancer Res.*, vol. 49, "Correlation between the effects of poly–amine analogues on DNA conformation and cell growth," Basu et al., pp. 5591–5597 (1989).

*Cancer Res.*, vol. 49, "Differential response to treatment with the bix(ethyl)polyamine analogues between human small cell lung carcinoma and undifferentiated large cell lung carcinoma in culture," Casero et al., pp. 639–643 (1988).

*Mol. Pharm.*, vol. 39, "Selective cellular depletion of mitochon–drial DNA by the polyamine analog, $N^1,N^{12}$–bis(ethyl)spermine, and its relationship to polyamine structure and function," Vertino et al., pp. 487–494 (1991).

*Biochem. and Biophys. Res. Comm.*, vol. 157, "Modulation of polyamine biosynthesis and transport by oncogene transfection," Chang et al., pp. 264–270 (1988).

*Biopolymers*, vol. 26, "Structural determinants of spermidine–DNA interactions," Vertino et al., pp. 691–703 (1987).

*J. Org. Chem.*, vol. 24, "Fluorine containing nitrogen compounds—I Trifluoroethylamines," Bissel et al., pp. 1256–1259 (1959).

*Proc. Am. Assoc. Cancer Res.*, vol. 49, "Differential induction of spermidine/spermine $N^1$–acetyltransferase in human lung cancer cells by the bis(ethyl)polyamine analogues," Casero et al., pp. 3829–3833 (1989).

*Proc. Am. Assoc. Cancer Res.*, vol. 30, "Potent induction of spermidine/spermine $N^1$–acetyltransferase (SSAT) activity and its relationship to inhibition of cell growth," Libby et al., p. 586 (1989).

*Biochem. Pharma.*, vol. 38, No. 9, "Structure–function correla–tions of polyamine analog–induced increases in spermidine/ spermine acetyltransferase activity," Libby et al., pp. 1435–1442 (1989).

Harada et al., Polyurethane foams, Chemical Abstracts, vol. 107:238203W (Dec. 28, 1997).

Kao Corp., Preparation of polyurethane foam, JP Kokai Tokkyo Koho JP 59 27,912 [84 27,912], Chemical Abstracts, vol. 101:112243s (Oct. 1, 1984).

Smirnova et al., Oligomeric N–methylated amides and amines, Chemical Abstracts, vol. 68:78586u (May 1968).

*Arch. Biochem. Biophys.*, vol. 284, Characterization of human spermidine/spermine $N^1$–acetyltransferse purified from cultured melanoma cells, Libby et al., pp. 238–244 (1991).

*Cancer Res.*, vol. 51, "Correlations between polyamine analog–induced increases in spermidine/spermine $N^1$–acetyltransferase activity and growth inhibition in human melanoma cell lines," Porter et al., pp. 3715–3720 (1991).

J. Biol. Chem., vol. 264, No. 20, "Effect of $N^1,N^{12}$–bis(ethyl)–spermine and related compounds on growth and polyamine acetyla–tion, content and excretion in human colon tumor cell," Pegg et al., pp. 11744–11749 (1989).

Clay et al., *Inorganic Chemistry*, vol. 24, No. 21, "Noncyclic Reference Ligands for Tetraaza Macrocycles. Synthesis and Thermodynamic Properties of a Series of alpha,omega–D-i–N–methylated Tetraaza Ligands and Their Copper (II) Complexes," pp. 3330–3336 (Oct. 9, 1985).

Glaser et al., *Biopolymers*, vol. 6, "Topography of Nucleic acid helices in solutions. III. Interactions of Spermine and Spermidine Derivatives with Polyadenylic–Polyuridylic and Polyinosinic–Polycytidylic Acid Helices," pp. 243–254 (1968).

* cited by examiner

1a-d
cis-, or trans-
1,4-, or 1,3-

2a-d
cis-, or trans-
1,4-, or 1,3-

|  |  |
|---|---|
| 4a-f | cis-, 1,4-, n=4; trans-, 1,4-, n=4 |
|  | cis-, 1,4-, n=3; trans-, 1,4-, n=3 |
|  | cis-, 1,3-, n=3; trans-, 1,3-, n=3 |

30%HBr-HOAc → NaOH → HCl
PhOH, CH$_2$Cl$_2$    H$_2$O/CHCl$_3$    EtOH

|  |  |
|---|---|
| 5a-f | cis-, 1,4-, n=4; trans-, 1,4-, n=4 |
|  | cis-, 1,4-, n=3; trans-, 1,4-, n=3 |
|  | cis-, 1,3-, n=3; trans-, 1,3-, n=3 |

ANALOGS OF BIOLOGICALLY ACTIVE, NATURALLY OCCURRING POLYAMINES, PHARMACEUTICAL COMPOSITIONS AND METHODS OF TREATMENT

RELATED APPLICATIONS

This appl is a continuation of Ser. No. 08/080,642 Jun. 22, 1993 U.S. Pat. No. 6,184,232, which is a continuation-in-part of application Ser. No. 07/834,345 filed Feb. 12, 1992, U.S. Pat. No. 5,342,945 which is a division of application Ser. No. 07/210,520 filed Jun. 23, 1988, U.S. Pat. No. 5,091,576, which is a continuation-in-part of application Ser. No. 07/066,227 filed Jun. 25, 1987 abandoned, which is a continuation-in-part of application Ser. No. 06/936,835 filed Dec. 2, 1986 abandoned.

Research leading to the completion of the invention was supported, in part, by Grant No. 2-U01-CA37606 awarded by the National Institutes of Health (NIH). The United States Government has certain rights in and to the invention claimed herein.

BACKGROUND OF THE INVENTION

1. Field of the Invention

The present invention relates to analogs of biologically active, naturally occurring polyamines having a wide variety of therapeutic properties, as well as pharmaceutical compositions containing the analogs and their use in methods of therapeutic treatment.

2. Discussion of the Prior Art

In recent years, a great deal of attention has been focussed on the polyamines, e.g., spermidine, norspermidine, homospermidine, 1,4-diaminobutane (putrescine) and spermine. These studies have been largely directed at the biological properties of the polyamines probably because of the role they play in proliferative processes. It was shown early on that the polyamine levels in dividing cells, e.g., cancer cells, are much higher than in resting cells. See Janne et al, A. Biochim. Biophys. Acta., Vol. 473, page 241 (1978); Fillingame et al, Proc. Natl. Acad. Sci. U.S.A., Vol. 72, page 4042 (1975); Metcalf et al, J. Am. Chem. Soc., Vol. 100, page 2551 (1978); Flink et al, Nature (London), Vol. 253, page 62 (1975); and Pegg et al, Polyamine Metabolism and Function, Am. J. Cell. Physiol., Vol. 243, pages 212–221 (1982).

Several lines of evidence indicate that polyamines, particularly spermidine, are required for cell proliferation: (i) they are found in greater amounts in growing than in non-growing tissues; (ii) prokaryotic and eukaryotic mutants deficient in polyamine biosynthesis are auxotrophic for polyamines; and (iii) inhibitors specific for polyamine biosynthesis also inhibit cell growth. Despite this evidence, the precise biological role of polyamines in cell proliferation is uncertain. It has been suggested that polyamines, by virtue of their charged nature under physiological conditions and their conformational flexibility, might serve to stabilize macromolecules such as nucleic acids by anion neutralization. See Dkystra et al, Science, Vol. 149, page 48 (1965); Russell et al, Polyamines as Biochemical Markers of Normal and Malignant Growth (Raven, New York, 1978); Hirschfield et al, J. Bacteriol., Vol. 101, page 725 (1970); Hafner et al, J. Biol. Chem., Vol. 254, page 12419 (1979); Cohn et al, J. Bacteriol., Vol. 134, page 208 (1978); Pohjatipelto et al, Nature (London), Vol. 293, page 475 (1981); Mamont et al, Biochem. Biophys. Res. Commun., Vol. 81, page 58 (1978); Bloomfield et al, Polyamines in Biology and Medicine (D. R. Morris and L. J. Morton, eds., Dekker, New York, 1981), pages 183–205; Gosule et al, Nature, Vol. 259, page 333 (1976); Gabbay et al, Ann. N.Y. Acad. Sci., Vol. 171, page 810 (1970); Suwalsky et al, J. Mol. Biol., Vol. 42, page 363 (1969); and Liquori et al, J. Mol. Biol., Vol. 24, page 113 (1968).

However, regardless of the reason for increased polyamine levels, the phenomenon can be and has been exploited in chemotherapy. See Sjoerdsma et al, Butterworths Int. Med. Rev.: Clin. Pharmacol. Thera., Vol. 35, page 287 (1984); Israel et al, J. Med. Chem., Vol. 16, page 1 (1973); Morris et al, Polyamines in Biology and Medicine, Dekker, New York, page 223 (1981); and Wang et al, Biochem. Biophys. Res. Commun., Vol. 94, page 85 (1980).

Because of the role the natural polyamines play in proliferation, a great deal of effort has been invested in the development of polyamine analogs as anti-proliferatives [Cancer Res., Vol. 49, "The role of methylene backbone in the anti-proliferative activity of polyamine analogues on L1210 cells," Bergeron et al, pages 2959–2964 (1989); J. Med. Chem., Vol. 31, "Synthetic polyamine analogues as antineoplastics," Bergeron et al, pages 1183–1190 (1988); Polyamines in Biochemical and Clinical Research, "Regulation of polyamine biosynthetic activity by spermidine and spermine—a novel antiproliferative strategy," Porter et al, pages 677–690 (1988); Cancer Res., Vol. 49, "Major increases in spermidine/spermine-$N^1$-acetyl transferase activity by spermine analogues and their relationship to polyamine depletion and growth inhibition in L1210 cells," Basu et al, pages 6226–6231 (1989); Biochem. J., Vol. 267, "Induction of spermidine/spermine $N^1$-acetyltransferase activity in Chinese-hamster ovary cells by $N^1,N^{11}$-bis(ethyl) norspermine and related compounds," Pegg et al, pages 331–338 (1990); Biochem. J., Vol. 268, "Combined regulation of ornithine and S-adenosylmethionine decarboxylases by spermine and the spermine analogue $N^1N^{12}$-bis(ethyl) spermine," Porter et al, pages 207–212 (1990); Cancer Res., Vol. 50, "Effect of $N^1,N^{14}$-bis(ethyl)-homospermine on the growth of U-87 MG and SF-126 on human brain tumor cells," Basu et al, pages 3137–3140 (1990); and Biochem. Biophys. Res. Commun., Vol. 152, "The effect of structural changes in a polyamine backbone on its DNA binding properties," Stewart, pages 1441–1446 (1988)]. These efforts have included the design of new synthetic methods [J. Org. Chem., Vol. 45, "Synthesis of $N^4$-acylated $N^1,N^8$-bis(acyl)spermidines: An approach to the synthesis of siderophores," Bergeron et al, pages 1589–1592 (1980); Synthesis, "Reagents for the selective acylation of spermidine, homospermidine and bis-[3-aminopropyl] amine," Bergeron et al, pages 732–733 (1981); Synthesis, "Reagents for the selective secondary functionalization of linear triamines," Bergeron et al, pages 689–692 (1982); Synthesis, "Amines and polyamines from nitriles," Bergeron et al, pages 782–785 (1984); J. Org. Chem., Vol. 49, "Reagents for the stepwise functionalization of spermidine, homospermidine and bis-[3-aminopropyl]amine," Bergeron et al, page 2997 (1984); Accts. Chem. Res., Vol. 19, "Methods for the selective modification of spermidine and its homologues," Bergeron, pages 105–113 (1986); Bioorg. Chem., Vol. 14, "Hexahydropyrimidines as masked spermidine vectors in drug delivery," Bergeron et al, pages 345–355 (1986); J. Org. Chem., Vol. 53, "Reagents for the stepwise functionalization of spermine," Bergeron et al, pages 3108–3111 (1988); J. Org. Chem., Vol. 52, "Total synthesis of (±)-15-Deoxyspergualin," Bergeron et al, pages 1700–1703 (1987); J. Org. Chem., Vol. 56, "The total synthesis of Alcaligin," Bergeron et al, pages 586–593 (1991); and CRC Handbook on Microbial Iron Chelates, "Synthesis of catecholamide and hydroxamate siderophores," Bergeron et al, pages 271–307 (1991)] for the production of these analogs, as well as extensive biochemical studies focussed on the mechanism by which these compounds act [*Cancer Res.*, Vol. 46, "A comparison and characterization of growth inhibition by α-Difluoromethylornithine (DFMO), and inhibitor of ornithine decarboxylase and $N^1,N^8$-bis(ethyl)spermidine (BES), an apparent regulator of the enzyme," Porter et al, pages 6279–6285 (1986); *Cancer Res.*, Vol. 47, "Relative abilities of bis(ethyl) derivatives of putrescine, spermidine and spermine to regulate polyamine biosynthesis and inhibit L1210 leukemia cell growth," Porter et al, pages 2821–2825 (1987); *Cancer Res.*, Vol. 49, "Correlation between the effects of polyamine analogues on DNA conformation and cell growth," Basu et al, pages 5591–5597 (1989); *Cancer Res.*, Vol. 49, "Differential response to treatment with the bis(ethyl)polyamine analogues between human small cell lung carcinoma and undifferentiated large cell lung carcinoma in culture," Casero et al, pages 639–643 (1988); *Mol. Pharm.*, Vol. 39, "Selective cellular depletion of mitochondrial DNA by the polyamine analog, $N^1,N^{12}$-bis(ethyl) spermine, and its relationship to polyamine structure and function," Vertino et al, pages 487–494 (1991); *Biochem. and Biophys. Res. Comm.*, Vol. 157, "Modulation of polyamine biosynthesis and transport by oncogene transfection," Chang et al, pages 264–270 (1988); and *Biopolymers*, Vol. 26, "Structural determinants of spermidine-DNA interactions," Vertino et al, pages 691–703 (1987)]. The mechanistic investigations have encompassed uptake studies, impact on polyamine analogs on polyamine pools and polyamine biosynthetic enzymes, as well as their effects on translational and transcriptional events.

Anti-neoplastic derivatives of the naturally occurring polyamines, pharmaceutical compositions and methods of treatment are also disclosed in the following pending patent application Ser. No. 08/231,692 filed Apr. 25, 1994, ("Sterically Hindered Tetraamines and Method for Their Production"), as well as in U.S. Pat. No. 5,091,576 issued Feb. 25, 1992; U.S. Pat. No. 5,128,353 issued, Jul. 7, 1992; and U.S. Pat. No. 5,173,505 issued Dec. 22, 1992. The disclosures of each of the foregoing applications and patents are incorporated herein by reference.

It is an object of the present invention to provide novel analogs of naturally occurring, biologically active polyamines which possess anti-neoplastic properties and to define the structural parameters which define compounds having such activities.

SUMMARY OF THE INVENTION

These and other objects are realized by the present invention, one embodiment of which relates to a polyamine having the formula:

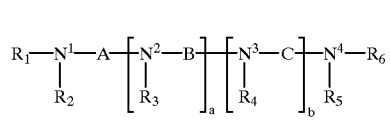

(I)

or a salt thereof with a pharmaceutically acceptable acid wherein:

$R_1$–$R_6$ may be the same or different and are alkyl, aryl, aryl alkyl, cycloalkyl, any of the foregoing wherein the alkyl chain is interrupted by at least one etheric oxygen atom, or hydrogen;

$N^1$, $N^2$, $N^3$ and $N^4$ are nitrogen atoms capable of protonation at physiological pH's;

a and b may be the same or different and are integers from 1 to 4;

A, B and C may be the same or different and are bridging groups which effectively maintain the distance between the nitrogen atoms such that the polyamine:

(i) is capable of uptake by a target cell upon administration of the polyamine to a human or non-human animal; and (ii) upon uptake by the target cell, competitively binds via an electrostatic interaction between the positively charged nitrogen atoms to substantially the same biological counter-anions as the intracellular natural polyamines in the target cell;

the polyamine, upon binding to the biological counter-anion in the cell, functions in a manner biologically different than the intracellular polyamines, the polyamine not occurring in nature.

Another embodiment of the invention comprises a pharmaceutical composition comprising an anti-neoplastic effective amount of the polyamine described above or a salt thereof with a pharmaceutically acceptable acid and a pharmaceutically acceptable carrier therefor.

An additional embodiment of the invention relates to a method of treating a human or non-human animal in need thereof comprising administering thereto an anti-neoplastic effective amount of the polyamine described above or a salt thereof with a pharmaceutically acceptable acid.

DETAILED DESCRIPTION OF THE INVENTION

Figure 1:
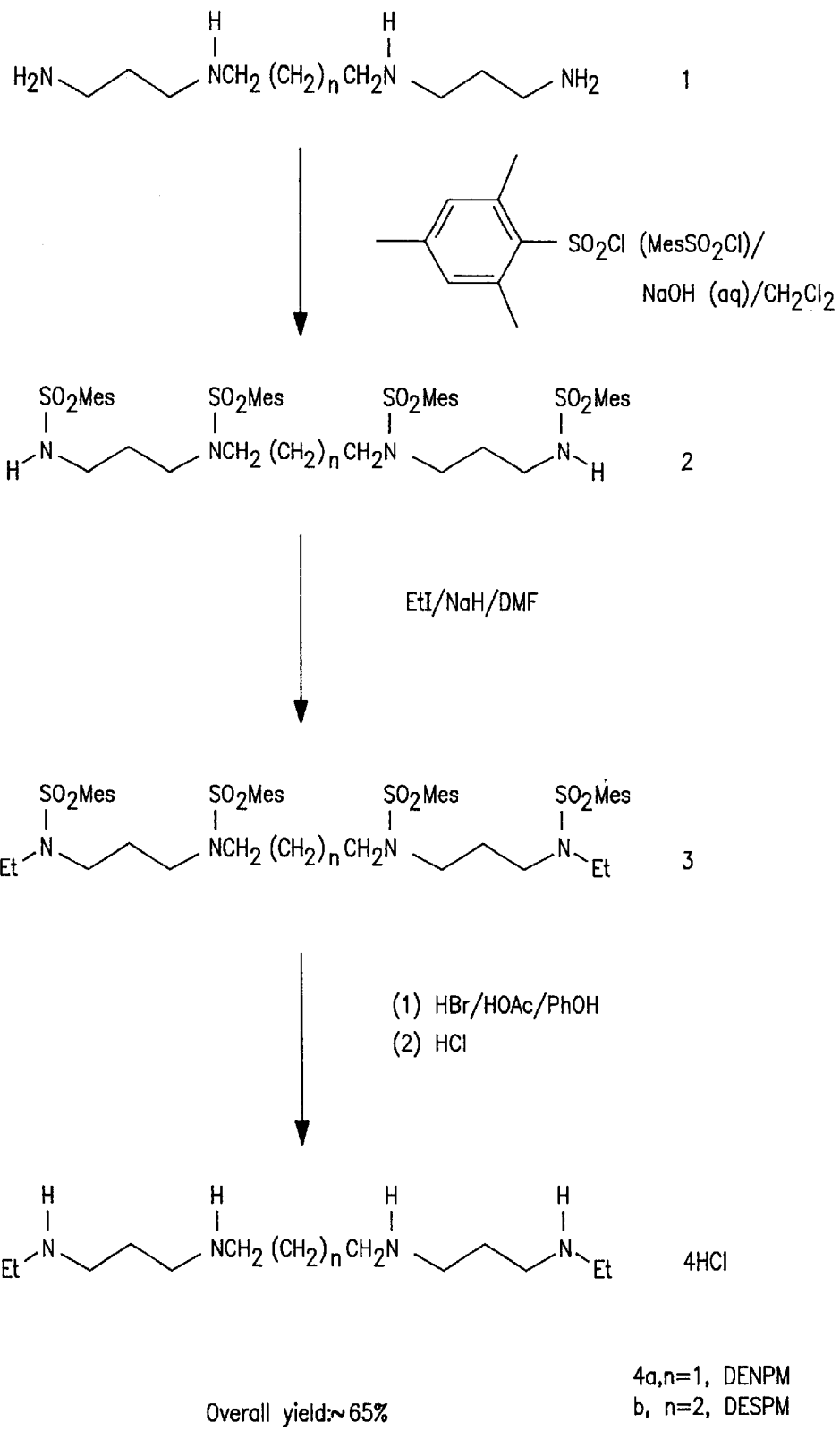
FIGS. 1–8 depict reaction schemes for preparing various of the polyamines of the invention and intermediates therefor.

In the polyamines of the invention, as described in the above structural formula, $R_1$–$R_6$ may be alkyl, e.g., methyl, ethyl, n-propyl, isopropyl, n-butyl, isobutyl, sec-butyl, tert-butyl; aryl, e.g., phenyl, p-tolyl, 2,4,6-trimethylphenyl; aryl alkyl, e.g., benzyl, α-phenethyl, β-phenethyl; cycloalkyl, e.g., cyclohexyl, cyclobutyl, cyclopentyl, cycloheptyl; any of the foregoing wherein the alkyl chain is interrupted by etheric oxygen, e.g., $CH_3O(CH_2)_2$—, $CH_3O(CH_2)_2O(CH_2)_2$—, $CH_3O(CH_2)_2O(CH_2)_2O(CH_2)_2$—; or hydrogen.

Except where $R_1$–$R_6$ are hydrogen or etheric substituents, each are hydrocarbyl and may have from about 1 to about 12 carbon atoms, it being understood that the size of the substituents will be tailored in each case to ensure that the polyamine is capable of uptake by the target cell and, upon uptake, will competitively bind with the intracellular counter-anions as described above.

The bridging groups A, B and C may be the same or different and may be alkylene having 1–8 carbon atoms, e.g., methylene, trimethylene, tetramethylene, pentamethylene; branched alkylene, e.g., —$CH(CH_3)CH_2CH_2$—, —$CH_2CH(CH_3)CH_2$—, —$CH(CH_3)CH_2CH_2$—, —$CH_2CH(CH_3)CH_2CH_2$—; arylalkylene, e.g., —$CH(Ph)CH_2CH_2$—, —$CH_2CH(Ph)CH_2$—, —$CH(Ph)CH_2CH_2CH_2$—, —$CH_2CH(Ph)CH_2$—$CH_2$—; cycloalkylene, e.g., cyclohexylene, cis- and trans-1,3-cyclohexylene, 1,4-cyclohexylene, 1,3-cyclopentylene; heterocyclic groups which incorporate within the ring one of the nitrogen atoms of the polyamine [e.g.,

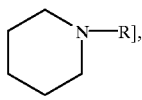

it being understood that the heterocyclic nitrogen group may be located at the terminal end(s) or within the interior of the polyamine.

Those skilled in the art will appreciate that it is only necessary that the bridging groups be selected so as to ensure uptake by the cell and competitive binding to the intracellular counter-anion as described above.

Particularly preferred polyamines are those set forth in Tables 1 and 2 and in the examples, as well as those having the formula:

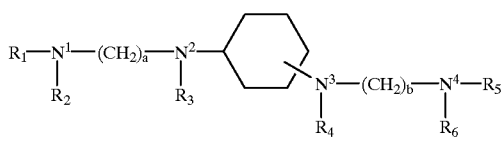

wherein $R_1$–$R_6$ have the meanings ascribed above and a and b may be the same or different and are integers from 2 to 8.

At physiological pH's, the naturally occurring polyamines and the analogs of the present invention are largely in a protonated state [*Bioorg. Chem.*, supra]. At a cellular level, these polycations can bind to a collection of single unconnected anions or to anions tethered to a single biomolecule, e.g., the phosphates on a nucleic acid.

If there is any significance to the role of charge interaction in the biological properties of the polyamine analogs, alterations in the polyamine methylene backbone should have significant impact on the compound's biological properties. In fact, the significance of charge and the length of the methylene bridges separating the cations in the biological properties of the polyamine analogs has been demonstrated. For example, although $N^1,N^{12}$-diethylspermine (DESPM) is quite active against a variety of tumors in cell culture, when the terminal ethyl groups are replaced by β,β,β-trifluoroethyl groups, the anti-neoplastic activity essentially disappears. The trifluoroethyl group substantially reduces the $pK_a$ of the terminal nitrogens and they are no longer protonated [*J. Org. Chem.*, Vol. 24, "Fluorine containing nitrogen compounds—I Trifluoroethylamines," Bissel et al, pages 1256–1259 (1959)]. Even though the dimensions of bis-β,β,β-trifluoroethylspermine and diethylspermine are essentially the same, what was once a tetracationic spermine analog is now only a dication. On comparing the abilities of several polyamines and polyamine analogs to displace ethidium iodide from calf thymus DNA, bis-β,β,β-trifluoroethylspermine (BTFESPM) was found to behave more like putrescine than spermine. The same phenomenon is observed when one acetylates a terminal nitrogen of spermine. The amide nitrogen is not protonated at physiological pH, and the compound has no anti-neoplastic properties and behaves very much like spermidine in displacing ethidium iodide from DNA.

Perhaps the most impressive finding regarding the separation of charge is associated with S-acetyltransferase (SAT), an enzyme responsible for the N-terminal acetylation of spermine and spermidine. It has been determined that very slight changes in the methylene backbone of the polyamine analogs have pronounced effects on up-regulating the production of this protein, diethylnorspermine (DENSPM)>diethylspermine (DESPM)>diethylhomospermine (DEHSPM) [*Proc. Am. Assoc. Cancer Res.*, Vol. 49, "Differential induction of spermidine/spermine $N^1$-acetyltransferase in human lung cancer cells by the bis(ethyl)polyamine analogues," Casero et al, pages 3829–3833 (1989); *Proc. Am. Assoc. Cancer Res.*, Vol. 30, "Potent induction of spermidine/spermine $N^1$-acetyltransferase (SSAT) activity and its relationship to inhibition of cell growth," Libby et al, page 586 (1989); *Biochem. Pharma.*, Vol. 38, No. 9, "Structure-function correlations of polyamine analog-induced increases in spermidine/spermine acetyltransferase activity," Libby et al, pages 1435–1442 (1989); *Cancer Res.*, Vol. 49, Basu et al, supra; *Biochem. J.*, Vol. 268, Porter et al, supra; *Biochem. J.*, Vol. 267, Pegg et al, supra; *Arch. Biochem. Biophys.*, Vol. 284, "Characterization of human spermidine/spermine $N^1$-acetyltransferase purified from cultured melanoma cells, Libby et al, pages 238–244 (1991); and *Cancer Res.*, Vol. 51, "Correlations between polyamine analog-induced increases in spermidine/spermine $N^1$-acetyltransferase activity and growth inhibition in human melanoma cell lines," Porter et al, pages 3715–3720 (1991)]. Extracting a single methylene from each of the three methylene bridges of DEHSPM substantially increases the ability of the analog to stimulate SAT up-regulation, DEHSPM has little impact on SAT levels, while DESPM up-regulates the enzyme by a factor of 200 and DENSPM by 1,200 fold. Although each of the tetraamines is a closely related linear tetracation at physiological pH, each provides a different signal to the cell. While DEHSPM has three 4-methylene bridges and little SAT-stimulating activity, DESPM which has a single central 4-methylene bridge and two terminal 3-methylene bridges is a more active SAT-stimulating factor. DENSPM has three 3-methylene bridges and is the most active SAT stimulator. Presumably, the cell then "reads the charge distribution" on the polyamines. This suggests that the key issue in the polyamine analogue's activity is the distance between the charged centers and not the nature of the groups separating these centers, "the insulators." However, that this was indeed the case required proof.

The total concentration of polyamines in cation equivalents, as well as the ratios of the various polyamines, is very tightly regulated and, when this equilibrium is disturbed, the cell acts quickly to re-adjust. For example, when polyamine analogs are incorporated, these dynamics are disrupted and the cell responds by either excreting polyamines in the free state or by first acetylating them, followed by excretion of the $N^1$-acetyl compounds [*J. Biol. Chem.*, Vol. 264, No. 20, "Effect of $N^1,N^{12}$-bis(ethyl) spermine and related compounds on growth and polyamine acetylation, content and excretion in human colon tumor cell," Pegg et al, pages 11744–11749 (1989); and *Cancer Res.*, Vol. 51, Porter et al, supra]. On analog incorporation, the cell disposes of the appropriate number of polyamine cation equivalents in order to maintain the total polyamine charge balance.

The analogs appear to the cell as normal polyamines and provide many of the same regulatory messages that the natural polyamines do. As analog concentration increases in the cell, the following events ensue. Polyamine biosynthesis is down-regulated, just as when cells are grown in exogenous polyamines. The levels of ornithine decarboxylase (ODC) and S-adenosylmethionine decarboxylase (AdoMETDC) are drastically reduced just as with the normal negative polyamine feedback control. Analogs with aminopropyl groups cause a marked increase in S-acetyl transferase (SAT). Once again, the issues are how the cell reads the charge distribution on the polyamines and how does it translate this information into regulatory events. The answers to both of these questions will allow one to define the structural boundary conditions for the general design of polyamine anti-neoplastics. Two fundamental issues needed to be addressed regarding the general structural requirements for anti-neoplastic polyamines: (1) Are the cationic centers really key to the compound's anti-neoplastic activity or are the nitrogen centers simply enough, and (2) what are the boundary conditions on the insulators, e.g., bridging groups separating the nitrogen or cationic centers?

The first question can be answered by comparing two polyamines with essentially the same distance between the nitrogens, but with different pKa values on spatially equivalent nitrogens. While the bis-β,β,β-trifluoroethyl analogue of $N^1,N^{12}$-diethylspermine strongly suggested that charge was significant in polyamine analogue activity, additional examples had to be developed. In particular, examples were utilized in which other than simple methylene insulators were employed. This experiment is typified by the compounds and their activities as set forth in Table 1.

TABLE 1

Piperidine and Pyridine Bicyclic Tetraamines

| Structure | $IC_{50}$ ($\mu$M) of L1210 cells at 48/96 h |
|---|---|
| [bis-piperidinylmethyl tetraamine structure] | 2/0.2 |
| [bis-pyridinylmethyl tetraamine structure] | >100/90 |
| [bis-piperidinylethyl tetraamine structure] | >100/0.25 |
| [bis-pyridinylethyl triamine structure] | >100/>100 |

The results of Table 1 clearly indicate that the nitrogen cationic centers are required for anti-neoplastic activity and not simply a nitrogen center. The pyridine compounds have their nitrogen separated by distances very similar to those in the corresponding piperidine systems. The major difference is, at physiological pH, the pyridine compounds are not substantially protonated at the pyridine nitrogens. This means that the piperidine compounds are tetracations at physiological pH, while the pyridines are dications. The dications, unlike the corresponding reduced and acyclic linear molecules, are not active against L1210 cells.

Whether the cations can be insulated from each other by other than a methylene bridge, e.g., a more rigid cyclic backbone, while still maintaining the activity of the compound is a question important not only to an understanding of how cells process information on the polycations, but also to the design of improved therapeutics. If a variety of other aliphatic systems can be substituted for the methylene bridges in the polyamines, it is possible to alter not only the metabolic properties of the polyamine anti-neoplastics, but also their organ distribution and clearance properties. The data set forth in Table 2 further indicates that simple linear insulators are not a strict requirement for polyamine analogue anti-neoplastic activity. The results suggest that the polyamine nitrogens can be incorporated into a cyclic backbone. This observation was further investigated to verify that nitrogen insulators could also be cyclic alkyl groups. Table 2 clearly indicates that this is true. The cyclohexyl fragment works well in a variety of different arrangements as an insulator.

in the molecules, they should be unable to be further processed. The inability of the polyamines to be further processed is largely related to the fact that the terminal nitrogens in the active compounds are alkylated and unable to be acetylated by SAT.

Linear Polyamine, Methylene Insulators

Previous synthetic methods [*J. Org. Chem.*, Vol. 45, Bergeron et al, supra; *Synthesis*, Bergeron et al (1981),

TABLE 2

| Analogue | L1210 I. C.$_{50}$ ($\mu$M) | | Ki ($\mu$M) |
| --- | --- | --- | --- |
| | 48 h | 96 h | |
| EtNH-(CH$_2$)$_4$-NH-cyclohexyl(trans)-NH-(CH$_2$)$_4$-NHEt·4HCl | 70 | 0.08 | 4.1 |
| EtNH-(CH$_2$)$_4$-NH-cyclohexyl(cis)-NH-(CH$_2$)$_4$-NHEt·4HCl | >100 | 0.3 | 1.5 |
| EtNH-(CH$_2$)$_3$-NH-cyclohexyl(trans)-NH-(CH$_2$)$_3$-NHEt·4HCl | >100 | 0.2 | 7.9 |
| EtNH-(CH$_2$)$_3$-NH-cyclohexyl(cis)-NH-(CH$_2$)$_3$-NHEt·4HCl | >100 | 0.6 | 1.8 |
| EtNH-(CH$_2$)$_3$-N(H)-cyclohexyl(cis-)-N(H)-(CH$_2$)$_3$-NHEt·4HCl | >100 | 3 | 30 |
| EtNH-(CH$_2$)$_3$-N(H)-cyclohexyl(trans)-NH-(CH$_2$)$_3$-NHEt·4HCl | >100 | 40 | n. a. |

The intention is that the cell should incorporate these compounds via the polyamine's transport apparatus and that these analogues should find their way to the same subcellular distribution sites that the naturally occurring polyamines do, but once there, because of subtle alterations supra; *Synthesis*, Bergeron et al (1982), supra; *Synthesis*, Bergeron et al (1984), supra; *J. Org. Chem.*, Vol. 49, Bergeron et al, page 2997 (1984); *Accts. Chem. Res.*, Vol. 19, Bergeron, supra; *Bioorg. Chem.*, Vol. 14, Bergeron et al, supra; *J. Org. Chem.*, Vol. 53, Bergeron et al, supra; *J. Org.*

Chem., Vol. 52, Bergeron et al, supra; *J. Org. Chem.*, Vol. 56, Bergeron et al, supra; and *CRC Handbook on Microbial Iron Chelates*, Bergeron et al, supra] were not designed for polyamine bridge expansions, but for the introduction of different alkyl groups at different nitrogens in the triamines or tetraamines. However, it has been recently shown that many of the simple terminally dialkylated polyamine analogs of interest can be accessed via the appropriate tosylamide. For example, to synthesize DESPM, spermine is first tosylated and then monoalkylated at each terminal tosylamide by treatment with sodium hydride and ethyl iodide. The tosyl groups are then removed under conditions of dissolving metal reduction. The shortcomings of the procedure are three-fold: (1) the alkylation must be symmetrical, i.e., the same alkyl group must be fixed to both terminal nitrogens, (2) the methylene insulators between the nitrogens are regulated by the availability of the starting polyamine, and (3) removal of the tosyl protecting group proceeds in low yield.

Figure 2:
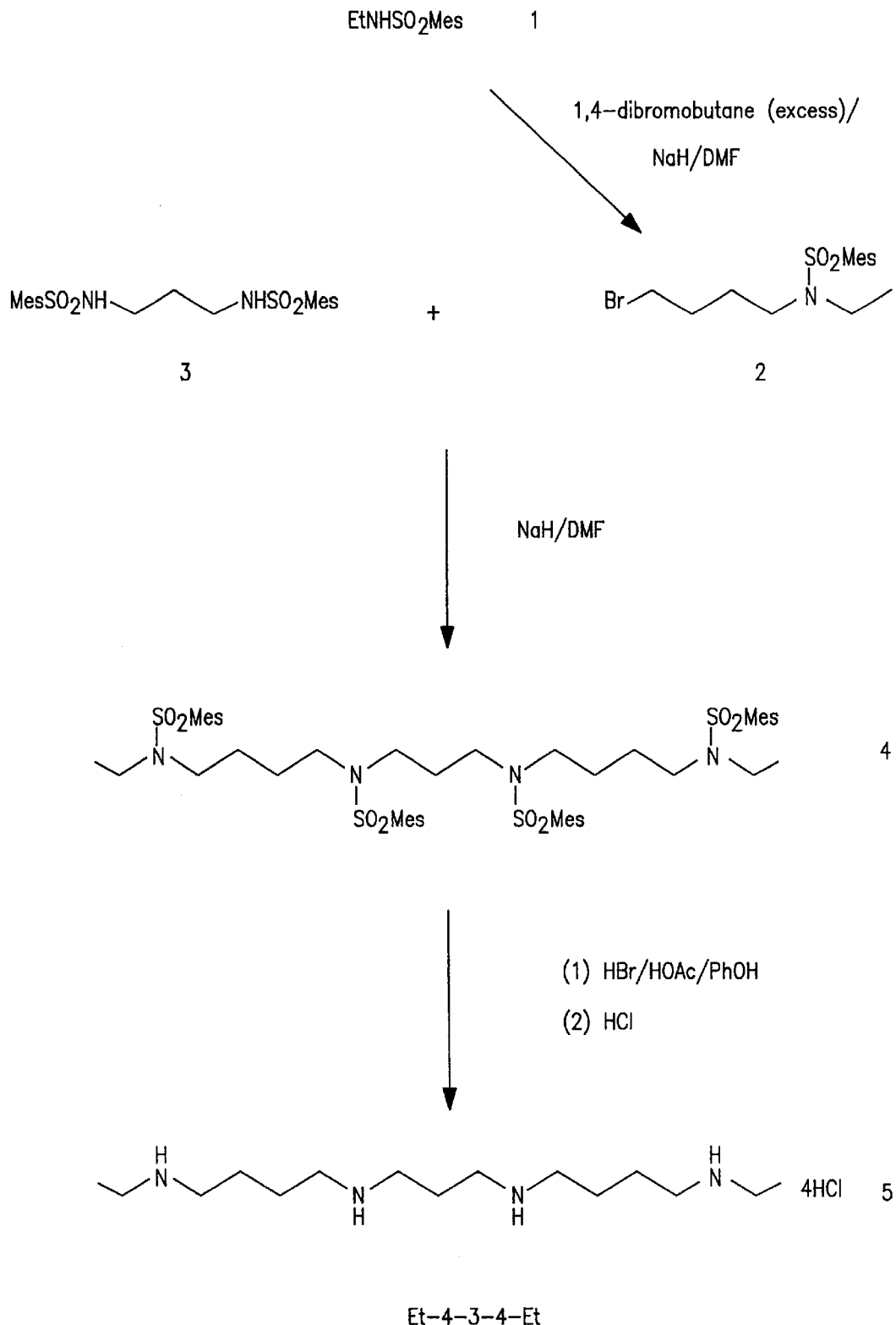

A more satisfactory alternative involves formation of the appropriate tetramesitylenesulfonamides, which can be alkylated in high yields and the tetramesitylenesulfonyl (MES) protecting groups quantitatively removed by treatment with 30% HBr in acetic acid and phenol (FIG. 1). This approach eliminates the low yield problem associated with removal of the tosyl protecting group under dissolving metal reduction conditions. The MES methodology has been extended to a symmetrical "segmented synthesis" which allows for the facile alteration of the methylene backbone (FIG. 2).

The segmented approach to constructing polyamine analogs offers numerous advantages in terms of flexibility and high yields. The procedure begins with mesitylenesulfonation of a primary amine providing (1), followed by alkylation of (1) with an excess of the appropriate dihalide (FIG. 2). The resulting halosulfonamide (2) can then be utilized to alkylate the disulfonamides, e.g., (3). The tetrasulfonamide (4) is treated with HBr/HOAc/PhOH to remove the mesitylenesulfonamide protecting groups. The resulting bromide is converted to the corresponding HCl salts. Thus, the limitations associated with the availability of the starting tetraamine have been eliminated, as well as removal of the tosyl protecting group. In addition, the earlier method was limited to terminal primary alkyl groups because of poor yields when alkylating with secondary and tertiary halides.

Linear Polyamine, Non-Methylene Insulators

Figure 3:
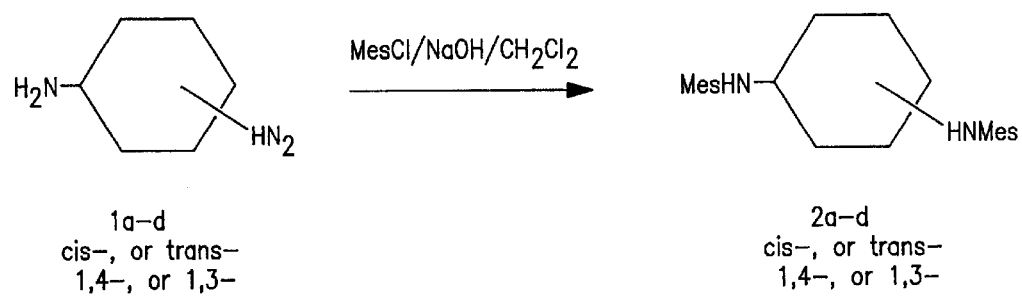
Figure 3:
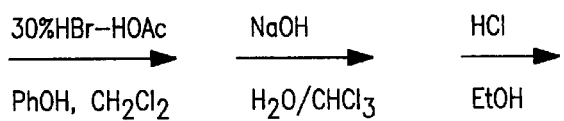
Figure 3:
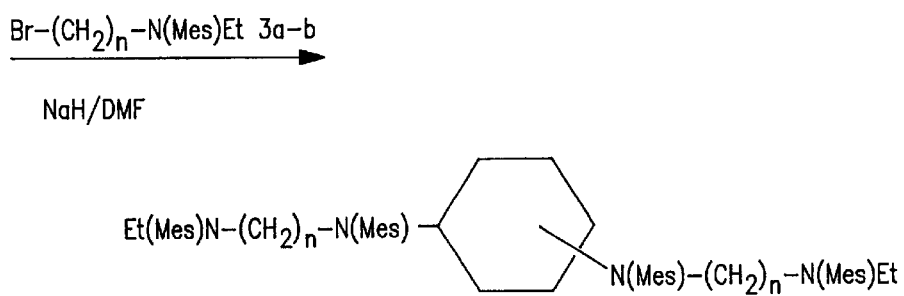
Figure 3:
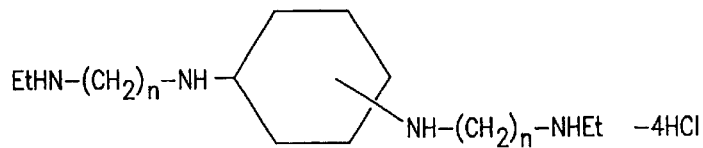

The above methodology has been successfully applied to the synthesis of, e.g., trans-1,4-diaminocyclohexane DESPM analog (FIG. 3). The cyclic disulfonamide (2) which is obtained by sulfonation of trans-1,4-cyclohexanediamine (1) is alkylated with two equivalents of halosulfonamide (3, n=3). Finally, the amine protecting groups of tetrasulfonamide (4) are easily removed by treatment with phenol and HBr as above to provide cyclic spermine analog (5).

Piperidine Polyamine Anti-Neoplastic Synthesis

Figure 4:
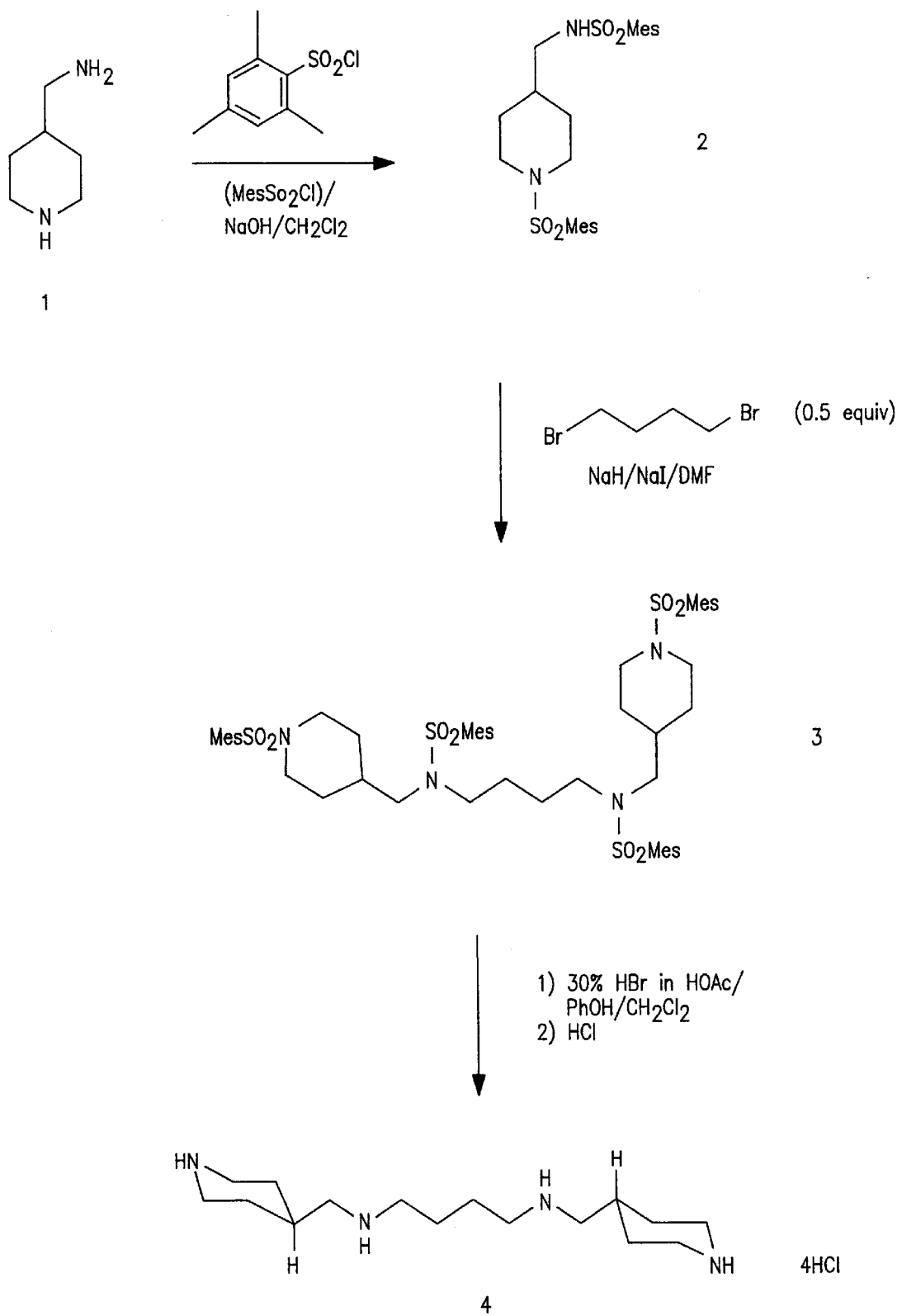
Figure 5:
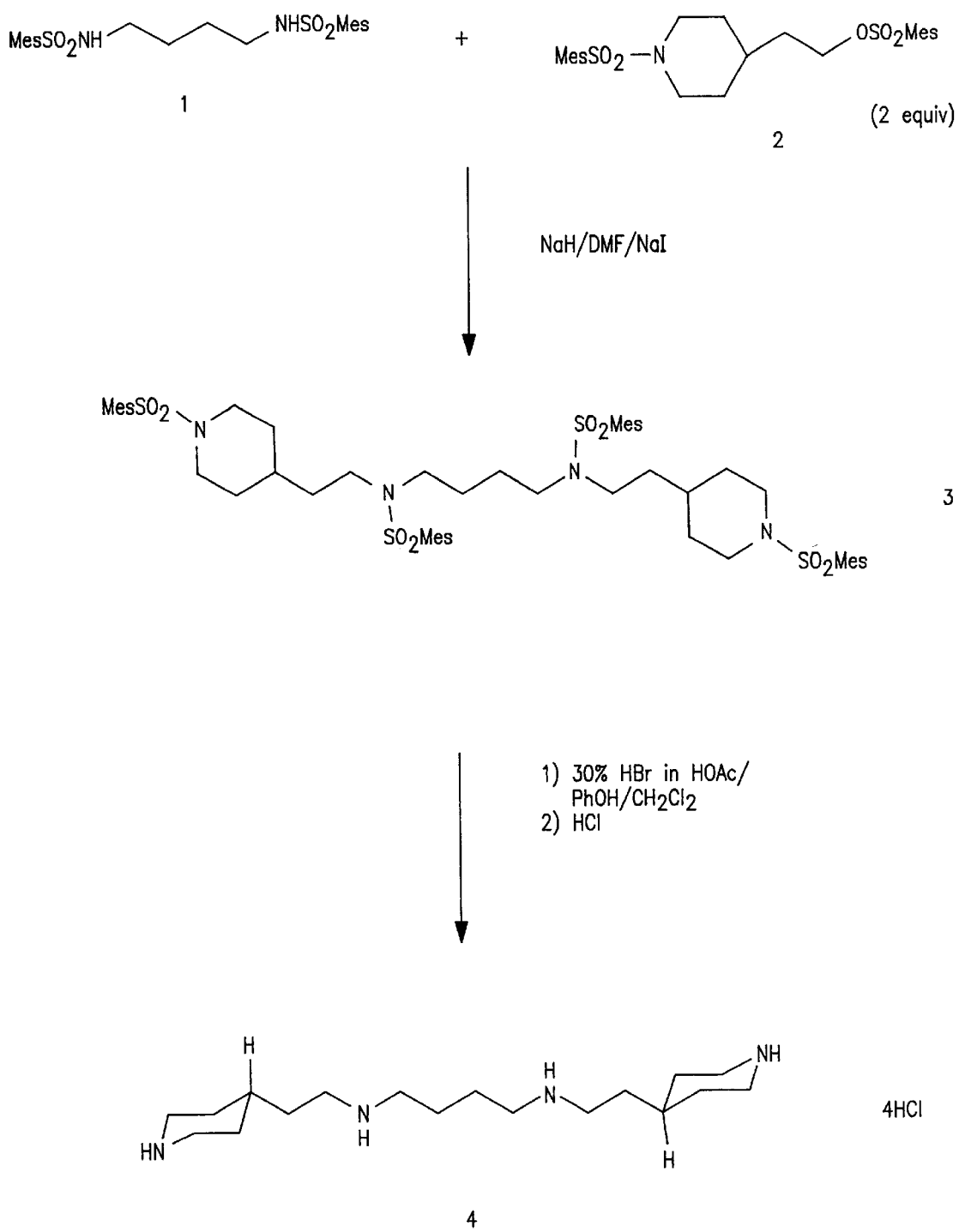

Tetraamines in which the terminal nitrogens are incorporated into piperidine rings can also be prepared using mesitylenesulfonyl-protected segments, as shown in FIGS. 4 and 5.

4-(Aminomethyl)piperidine (1) was converted into bis-sulfonamide (2) which was alkylated with 1,4-dibromobutane (0.5 equivalent)/NaH/DMF to complete the polyamine framework (3). Reductive removal of the sulfonamide protecting groups in (3) was accomplished with 30% HBr in HOAc/PhOH, generating bicyclic DEHSPM analog (4) (FIG. 4).

The corresponding 5-4-5 bicyclic polyamine was synthesized from the inside out (FIG. 5). Crystalline N,N'-bis (mesitylenesulfonyl)putrescine (1) was alkylated at both ends with mesitylenesulfonate (2), a solid derived from 4-piperidineethanol and mesitylenesulfonyl chloride ($MesSO_2Cl$) in pyridine. Deprotection of sulfonamide (3) with HBr as usual gave the larger bicyclic spermine homolog (4).

Synthesis of Unsymmetrical Polyamine Anti-Neoplastics

Figure 6:
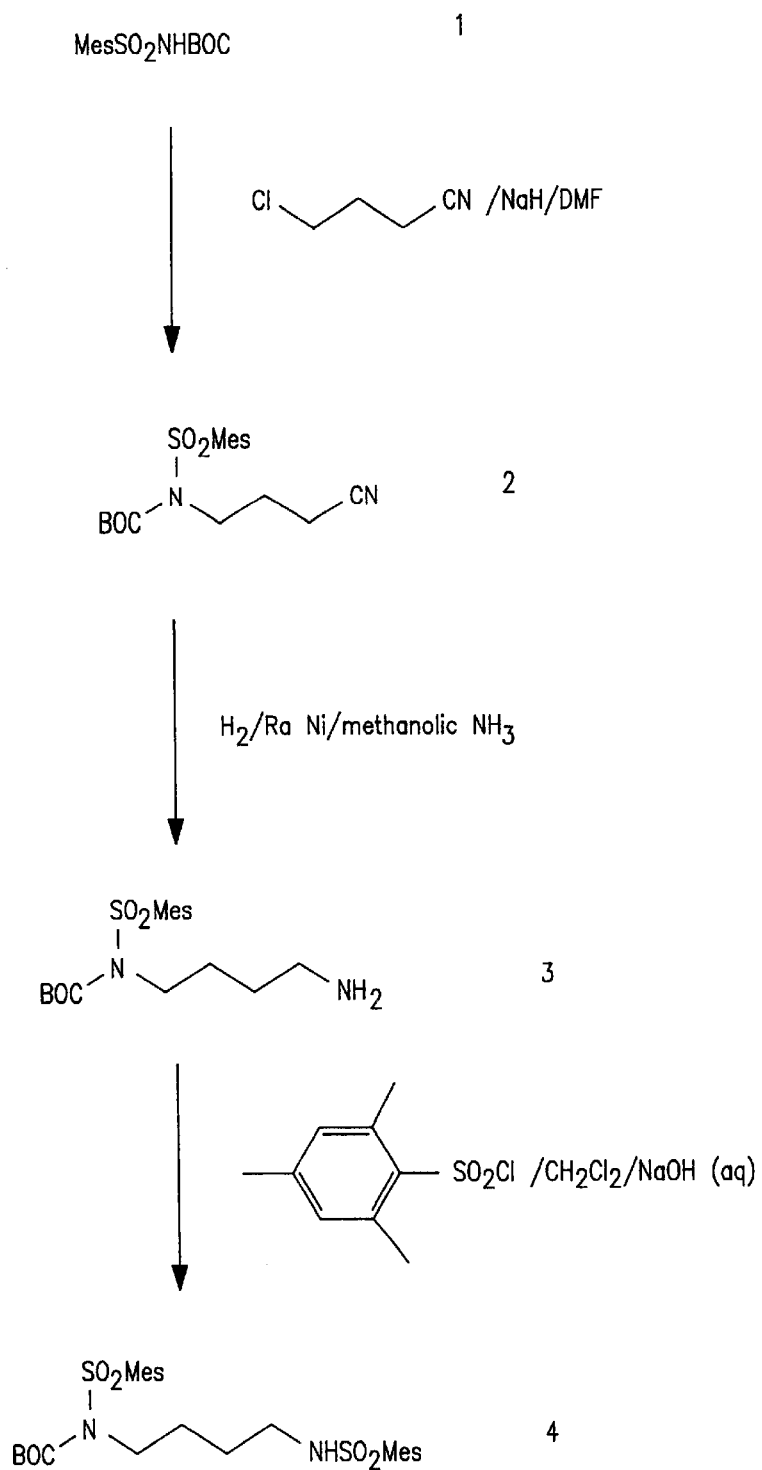

The development of a tri-protected diamine reagent (FIG. 6) permits the efficient synthesis of tetraamines which are unsymmetrical with respect to both their outer methylene chains and terminal alkyl substituents. This methodology eliminates the limitation in earlier routes that the terminal alkyl substituents must be identical. Furthermore, terminal monoethyl polyamines (FIG. 8), which are useful as standards in studies of diethyl analog metabolism, can also be generated in a systematic way.

N-(tert-Butoxycarbonyl)-N-mesitylenesulfonylamide ($BOCNHSO_2Mes$) (1), a di-protected ammonia, was alkylated with 4-chlorobutyronitrile (NaH/DMF) to give (2). The cyano group of (2) was hydrogenated with Raney nickel in methanolic ammonia, resulting in primary amine (3). Both the tert-butoxycarbonyl and mesitylenesulfonyl amine protecting groups were stable to these reduction conditions. Attachment of a second mesitylenesulfonyl functionality to amine (3) under bi-phasic conditions generated the reagent, N-(tert-butoxycarbonyl)-N,N'-bis(mesitylenesulfonyl) putrescine (4). It is noteworthy that this route is flexible, as well, in that an ω-chloroalkanenitrile of any length can be employed in the alkylation of $BOCNHSO_2Mes$ (1).

Figure 7:
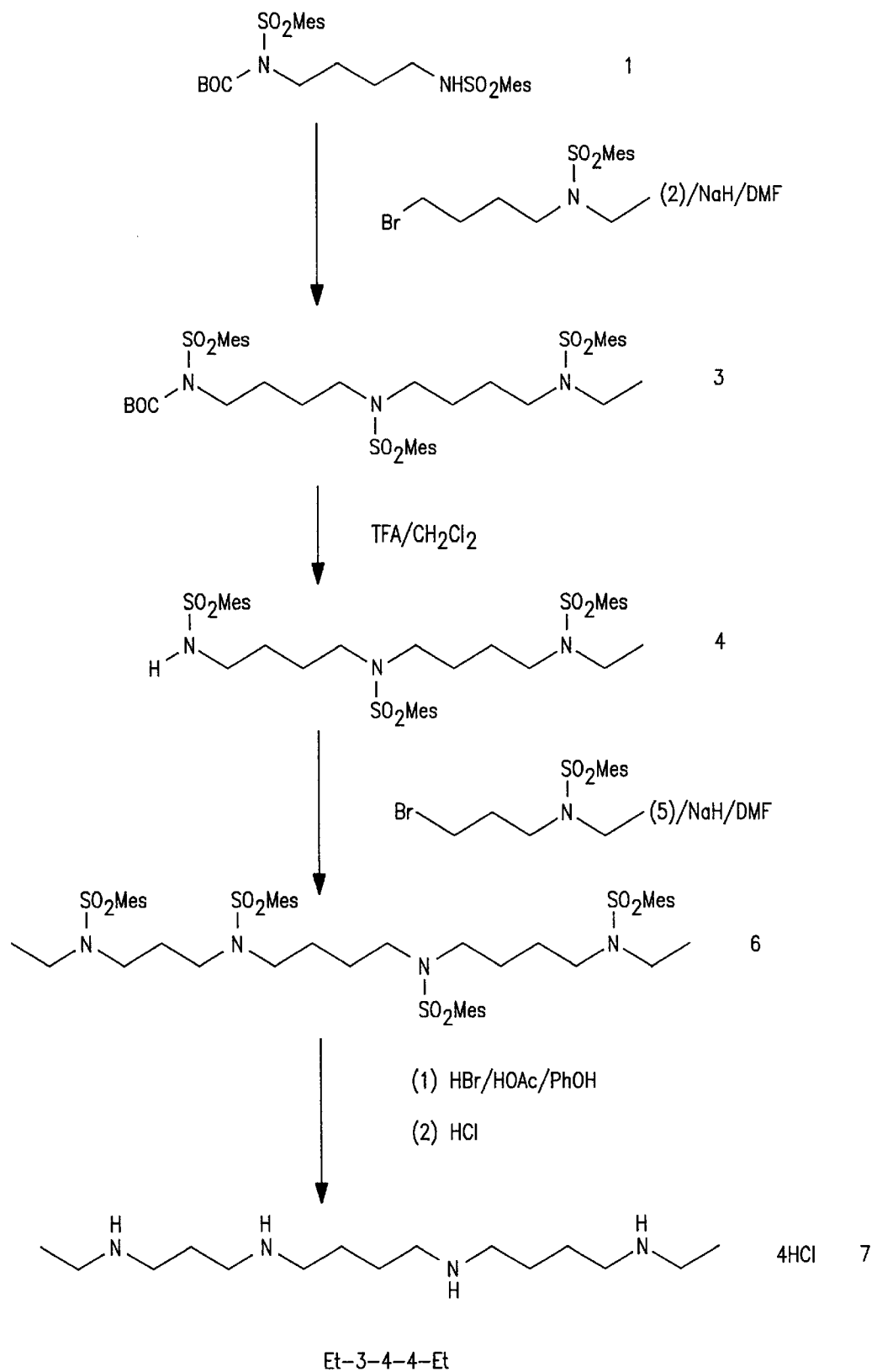
Figure 8:
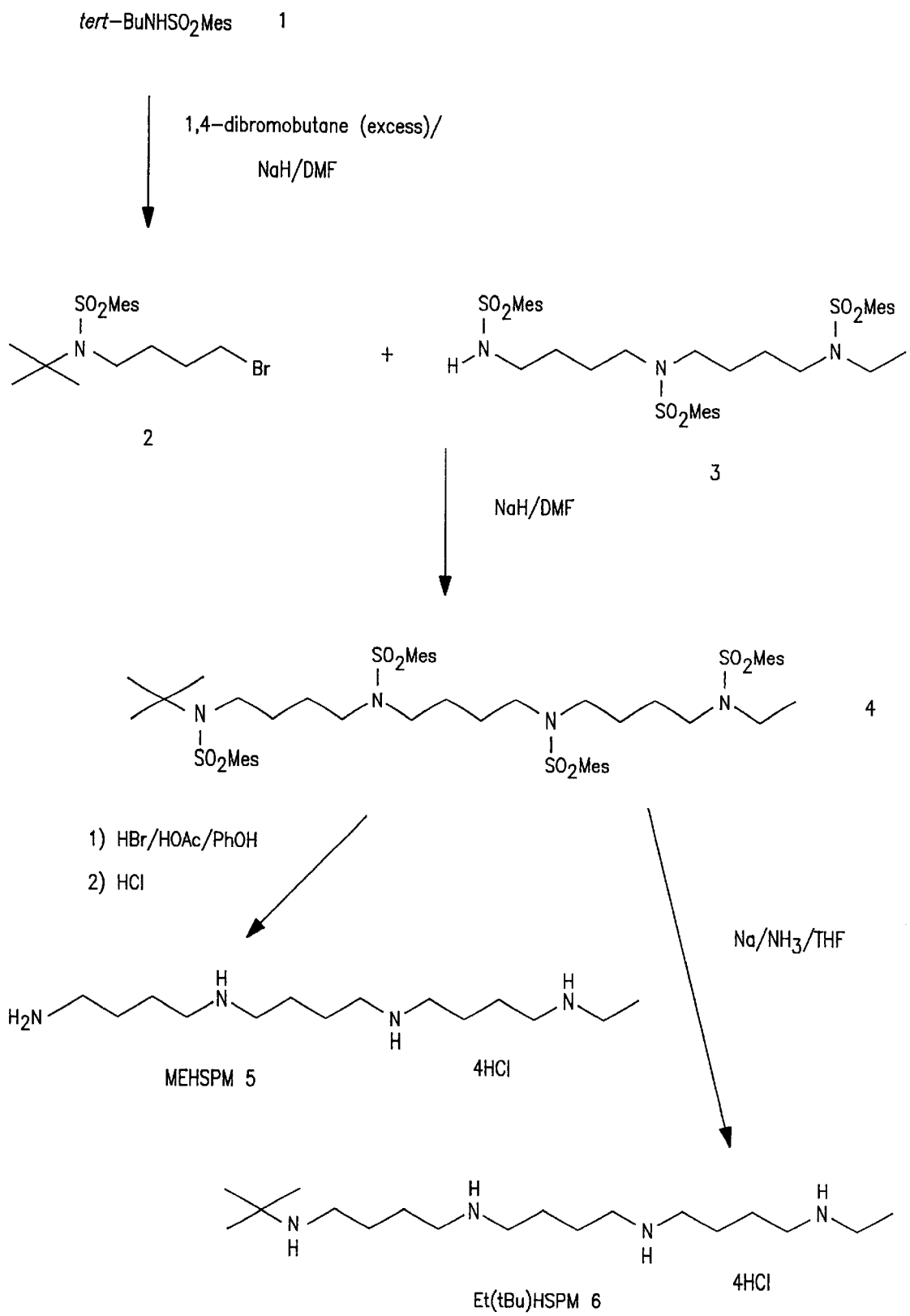

Applications of the tri-protected diamine reagent to unsymmetrical polyamine preparation are shown in FIGS. 7 and 8. Reagent (1) was deprotonated and alkylated with N-(ethylamino)tetramethylene unit (2), providing (3) (FIG. 7). After removal of the tert-butoxycarbonyl group under mild acidic conditions (TFA, $CH_2Cl_2$) to produce (4), the other nitrogen of the putrescine reagent was elaborated with N-(ethylamino)trimethylene segment (5). Unmasking of the amino groups of (6) generated tetraamine (7), in which the outer chains are unequal.

N-Ethyl trisulfonamide (3) (FIG. 8) was alkylated with N-(4-bromobutyl)-N-(tert-butyl) mesitylenesulfonamide (2) to afford masked polyamine (4). Treatment of (4) with HBr/HOAc/PhOH cleanly removed the tert-butyl group, as well as the sulfonamides, giving $N^1$-ethylhomospermine (5), a polyamine analog metabolite. Only the sulfonamides were cleaved using sodium and liquid ammonia to provide the unsymmetrically dialkylated homospermine derivative (6).

The invention is illustrated by the following non-limiting examples.

EXAMPLE 1

Bis-N,N'-(2-mesitylenesulfonyl)-trans-1,4-cyclohexanediamine [(2a) FIG. 3]

A solution of 2-mesitylenesulfonyl chloride (12.15 g, 55.0 mmol) in 100 ml $CH_2Cl_2$ was slowly dripped into a solution of trans-1,4-diaminocyclohexane (2.92 g, 25.0 mmol) in 100 ml 1 N NaOH solution, which had been cooled to 0° C. The mixture was stirred at 0° C. for 30 min. and at room temperature overnight. The solid was filtered out and washed with water and ethanol, to give 10 g (2a) (82%): mp>300° C.; NMR DMSO-$d_6$) δ0.97–1.23 (m, 4H), 1.40–1.63 (m, 4H), 2.20 (s, 6H), 2.50 (s, 12H), 2.63–2.83 (m, 2H).

N-Ethyl-N-(4-bromobutyl)mesitylenesulfonamide [(3b) FIG. 3]

NaH (0.792 g, 80%, 26.4 mmol) was added into a solution of N-ethyl-(2-mesitylenesulfonylamide) (5 g, 22.0 mmol) in 60 ml DMF, which had been cooled to 0° C. The mixture was stirred at 0° C. for 30 min., and 1,4-dibromobutane (31.5 ml, 261.4 mmol) was added. The solution was warmed to room temperature for 30 min. and then heated to 80° C. overnight. The DMF was removed, and the residue was treated with 40 ml water, followed by the extraction with $CH_2Cl_2$ (50 ml×4). The extractions were dried over anhydrous sodium sulfate, and the solvent was rotovapped. The crude oil was purified by silica gel column chromatography with 10/1 hexanes/EtOAc as an eluant, to provide 5.85 g (3b) (73%) as an oil; NMR (CDCl$_3$) δ1.07 (t, J=12, 3H), 1.60–1.83 (m, 4H), 2.27 (s, 3H), 2.57 (s, 6H), 3.07–3.37 (m, 6H), 6.90 (s, 2H). Anal. calcd. for $C_{15}H_{24}BrNO_2$: C, 49.73; H, 6.68; N, 3.87. Found: C, 49.78; H, 6.72; N, 3.88.

N,N'-Bis{4-[N"-ethyl,N"(2-mesitylenesulfonyl)]aminobutyl}-trans-1,4-N,N'-bis[(2-mesitylenesulfonyl)amino]cyclohexane [(4a) FIG. 3]

NaH (206.6 mg, 80%, 6.89 mmol) was added into a solution of (2a) (1.5 g, 3.13 mmol) in 40 ml DMF, which had been cooled to 0° C. The solution was stirred at 0° C. for 30 min., and the solution of (3b) (2.5 g, 6.89 mmol) in 20 ml DMF was slowly added at 0° C. Then the mixture was stirred at 0° C. for 20 min., room temperature for 30 min. and 70° C. overnight, respectively, following the procedure of (3b) above, the residue of which was purified by column chromatography with 5% ethanol in chloroform as an eluant, to give 0.93 g (4a) (29%) as an oil; NMR (CDCl$_3$) 1.00 (t, J=12, 6H), 1.13–1.43 (m, 4H), 1.73–1.93 (m, 4H), 2.27 (s, 12H), 2.57 (s, 24H), 2.83–3.23 (m, 12H), 3.35–3.67 (m, 2H), 6.90 (s, 8H). Anal. calcd. for $C_{52}H_{76}N_4O_8S_4$: C, 61.63, H, 7.56, N, 5.53. Found: C, 61.72, H, 7.59, N, 5.56.

N,N'-Bis[4-(N"-ethylamino)butyl]trans-1,4-cyclohexanediamine tetrahydrochloride [(5a) FIG. 3]

Phenol (2 g, 21.3 mmol) and 20 ml 30% HBr—HOAc were added into a solution of (4a) (720 mg, 0.69 mmol) in 25 ml $CH_2Cl_2$, and the solution was stirred at room temperature for 24 hours. The solution was diluted with 60 ml H$_2$O, and the $CH_2Cl_2$ layer was separated from the aqueous layer and the aqueous layer was washed by $CH_2Cl_2$ (40 ml×5). The water was removed, and the residue was dissolved in 10 ml H$_2$O, basified to pH>12 by the NaOH solution, extracted by CHCl$_3$ (40 ml×5) and dried over sodium sulfate. The salt was filtered out and the solvent was rotovapped. The oil was dissolved in 50 ml EtOH, and 1 ml concentrated HCl acid was added. The EtOH was removed and 320 mg crude solid was recrystallized from the mixture of H$_2$O and EtOH to produce 127 mg (5a) (40%) as nice crystal. NMR (D$_2$O) 1.30 (t, J=12, 6H), 1.50–1.67 (m, 4H), 1.67–1.97 (m, 8H), 2.07–2.40 (m, 4H), 2.90–3.40 (m, 14H). Anal. calcd. for $C_{18}H_{44}Cl_4N_4$: C, 47.17, H, 9.68, N, 12.22. Found: C, 47.01, H, 9.67, N, 12.13.

EXAMPLE 2

N,N'-Bis(2,4,6-trimethylbenzenesulfonyl)-4-(aminomethyl)piperidine [(2) FIG. 4]

A solution of 2-mesitylenesulfonyl chloride (19.49 g, 89.1 mmol) in $CH_2Cl_2$ (100 ml) was added to 4-(aminomethyl)piperidine (1) (5.15 g, 45.1 mmol) in 1 N NaOH (100 ml) at 0° C. After the addition was complete, the biphasic mixture was stirred for 24 hours (0° C. to room temperature). The layers were separated and the aqueous portion was extracted with CHCl$_3$ (2×). The combined organic phase was washed with 0.5 N HCl (200 ml) and H$_2$O (100 ml), dried with sodium sulfate and evaporated in vacuo. Recrystallization from aqueous ethanol produced 18.72 g (88%) of (2) as plates: mp 158.5–160° C.; NMR (CDCl$_3$/TMS) δ0.8–2.0 (m, 5H), 2.25 (s, 6H), 2.46–2.93 (m+2s, 16H), 3.37–3.65 (m, 2H), 4.67 (t, 1H, J=6), 6.90 (s, 4H). Anal. calcd. for $C_{24}H_{34}N_2O_4S_2$: C, 60.22, H, 7.16, N, 5.85. Found: C, 60.31, H, 7.19, N, 5.86.

N,N'-1,4-Bis(2,4,6-trimethylbenzenesulfonyl)butanediylbis[4-(2,4,6-trimethylbenzenesulfonyl)piperidinemethanamine [(3) FIG. 4]

Sodium hydride (80% in oil, 1.411 g, 47.0 mmol) was added to (2) (18.43 g, 38.5 mmol) and NaI (0.146 g, 0.97 mmol) in DMF (165 ml) at 0° C. The suspension was stirred for 1¾ hours at room temperature under nitrogen. 1,4-Dibromobutane (2.2 ml, 18.4 mmol) was added by syringe, and the reaction mixture was heated at 84° C. for 19 hours. After cooling to 0° C., H$_2$O (200 ml) was cautiously added to quench residual NaH, followed by extraction with CHCl$_3$ (300 ml, 2×100 ml). The combined organic phase was washed with 1% Na$_2$SO$_3$ (100 ml) and H$_2$O (2×100 ml), dried with sodium sulfate and evaporated under high vacuum. Recrystallization from EtOAc/CHCl$_3$ gave 13.00 g (70%) of (3) as an amorphous solid: mp 202–203.5° C.; NMR (CDCl$_3$/TMS) δ0.75–1.90 (m, 14H), 2.25 (s, 12H), 2.40–3.18 (m+2s, 36H), 3.3–3.6 (m, 4H), 6.87 (s, 8H). Anal. calcd. for $C_{52}H_{74}N_4O_8S_4$: C, 61.75, H, 7.37, N, 5.54. Found: C, 61.49, H, 7.39, N, 5.43.

N,N'-1,4-Butanediylbis(4-piperidinemethanamine) [(4) FIG. 4]

30% HBr in acetic acid (100 ml) was added over 10 min. to a solution of (3) (5.34 g, 5.28 mmol) and phenol (18.97 g, 0.202 mol) in $CH_2Cl_2$ (75 ml) at 0° C. The reaction was stirred for 24 hours (0° C. to room temperature) and cooled to 0° C. Distilled H$_2$O (120 ml) was added, followed by extraction with $CH_2Cl_2$ (3×100 ml). The aqueous layer was evaporated under high vacuum. The residue was basified with 1 N NaOH (12 ml) and 50% (w/w) NaOH (20 ml) with ice cooling, followed by extraction with CHCl$_3$ (10×50 ml), while adding NaCl to salt out the aqueous layer. Organic extracts were dried with sodium sulfate and evaporated. The residue was taken up in ethanol (200 ml), acidified with concentrated HCl (3.5 ml) and solvents were removed under vacuum. Tetrahydrochloride salt was recrystallized with 7% aqueous EtOH to furnish 1.318 g (58%) of (4) as a white solid. NMR (D$_2$O/TSP) δ1.19–2.23 (m, 14H), 2.8–3.6 (m, 16H). Anal. calcd. for $C_{16}H_{38}Cl_4N_4$: C, 44.87, H, 8.94, N, 13.08. Found: C, 44.77, H, 9.00, N, 13.00.

EXAMPLE 3

N,N'-Bis(2,4,6-trimethylbenzenesulfonyl)-1,4-butanediamine [(1) FIG. 5]

2-Mesitylenesulfonyl chloride (54.40 g, 0.249 mol) in $CH_2Cl_2$ (300 ml) was added to 1,4-diaminobutane (11.34 g, 0.129 mol) in 1 N NaOH (300 ml) at 0° C., and the biphasic mixture was stirred for 24 hours at room temperature. Organic solvent was evaporated and 2.4 N HCl (250 ml) was added to the combined portions. Solid was filtered, washed with water (250 ml) and recrystallized from aqueous ethanol to give 50.46 g (90%) of (1) as needles: mp 156.5–157.5° C.; NMR (CDCl$_3$/TMS) δ1.36–1.60 (m, 4H), 2.27 (s, 6H), 2.57 (s, 12H), 2.69–2.96 (m, 4H), 4.65 (t, 2H, J=6), 6.89 (s, 4H).

Anal. calcd. for $C_{22}H_{32}N_2O_4S_2$: C, 58.38, H, 7.13, N, 6.19. Found: C, 58.31, H, 7.19, N, 6.14.

N,O-Bis(2,4,6-trimethylbenzenesulfonyl)-4-piperidineethanol [(2) FIG. 5]

2-Mesitylenesulfonyl chloride (24.78 g, 0.113 mol) in pyridine (60 ml) was added all at once to 4-piperidineethanol (5.58 g, 43.2 mmol) in pyridine (25 ml) at −16° C.; the temperature rose to −11° C. The flask was stored in the refrigerator at 5.5° C. for 44 hours under argon. The reaction mixture was poured into ice (1 kg) and after 3 hours, 16.00 g (75%) of (2) as a yellow solid was filtered off: mp 93.5–94° C.; NMR (CDCl$_3$/TMS) δ1.4–2.1 (m, 7H), 2.27 (s, 6H), 2.44–2.96 (m+s, 14H), 3.37–3.69 (m, 2H), 3.97 (t, 2H, J=5), 6.90 and 6.93 (2s, 4H). Anal. calcd. for $C_{25}H_{35}NO_5S_2$: C, 60.82, H, 7.15, N, 2.84. Found: C, 60.90, H, 7.13, N, 2.85.

N,N'-1,4-Bis(2,4,6-trimethylbenzenesulfonyl) butanediylbis[4-(2,4,6-trimethylbenzenesulfonyl) piperidineethanamine [(3) FIG. 5]

Sodium hydride (80% in oil, 0.783 g, 26.1 mmol) was added to (1) (5.15 g, 11.4 mmol) and NaI (0.376 g, 2.5 mmol) in DMF (140 ml) at 0° C. The suspension was stirred for 23 min. at room temperature, followed by the introduction of (2) (15.84 g, 32.1 mmol). The reaction mixture was heated at 58–67° C. for 18 hours and then poured into H$_2$O (300 ml), followed by extraction with CHCl$_3$ (4×100 ml). The combined extracts were washed with saturated NaHCO$_3$ (100 ml), 1% NaHSO$_3$ (100 ml) and H$_2$O (100 ml), dried with sodium sulfate and evaporated under high vacuum. Column chromatography on silica gel eluting with 1 to 2% CH$_3$OH/CHCl$_3$ furnished 10.03 g (85%) of (3) as an amorphous solid: NMR (CDCl$_3$/TMS) δ0.8–2.0 (m, 18H), 2.08–2.71 (m+3s, 40H), 2.8–3.5 (m, 12H), 6.87 (s, 8H). Anal. calcd. for $C_{54}H_{78}N_4O_8S_4 \cdot H_2O$: C, 61.33, H, 7.62, N, 5.30. Found: C, 61.50, H, 7.44, N, 5.33.

N,N'-1,4-Butanediylbis(4-piperidineethanamine [(4) FIG. 5]

30% HBr in acetic acid (180 ml) was added over 30 min. to a solution of (3) (9.83 g, 9.45 mmol) and phenol (33.38 g, 0.355 mol) in CH$_2$Cl$_2$ (135 ml) at 0° C. The reaction was stirred for 24 hours (0° C. to room temperature) and cooled to 0° C. Distilled H$_2$O (200 ml) was added, followed by extraction with CH$_2$Cl$_2$ (2×100 ml). The aqueous portion was evaporated under high vacuum. The residue was basified with 1 N NaOH (50 ml) and then 50% (w/w) NaOH (10 ml) (ice cooling), followed by extraction with CHCl$_3$ (10×), while adding NaCl to salt out the aqueous layer. Organic extracts were dried over sodium sulfate and evaporated. Concentrated HCl (5 ml) in ethanol (300 ml) was added to the residue, and solvents were removed under vacuum. Tetrahydrochloride salt was recrystallized in 3% aqueous EtOH to give 2.91 g (68%) of (4) as a white solid: NMR (D$_2$O/TSP) δ1.15–2.09 (m, 18H), 2.75–3.59 (m, 16H). Anal. calcd. for $C_{18}H_{42}Cl_4N_4$: C, 47.37, H, 9.28, N, 12.28. Found: C, 47.25, H, 9.35, N, 12.17.

I claim:

1. A polyamine having the formula:

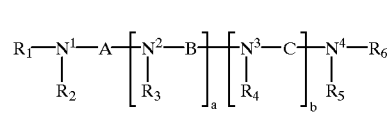

(I)

or a salt thereof with a pharmaceutically acceptable acid wherein:

$R_1$–$R_6$ may be the same or different and are alkyl, aryl, aryl alkyl, cycloalkyl, optionally having an alkyl chains interrupted by at least one etheric oxygen atom, or hydrogen $N^1$, $N^2$, $N^3$ and $N^4$ are nitrogen atoms capable of protonation at physiological pH's;

a and b may be the same or different and are integers from 1 to 4;

A, B and C may be the same or different and are bridging groups which effectively maintain the distance between said nitrogen atoms such that said polyamine:
(i) is capable of uptake by a target cell upon administration of said polyamine to a human or non-human animal; and
(ii) upon uptake by said target cell, competitively binds via an electrostatic interaction between the positively charged nitrogen atoms to substantially the same biological counter-anions as the intra-cellular natural polyamines in the target cell;

said polyamine, upon binding to said biological counter-anion in the cell, functions in a manner biologically different than said intracellular polyamines, said polyamine not occurring in nature.

2. A polyamine having the formula:

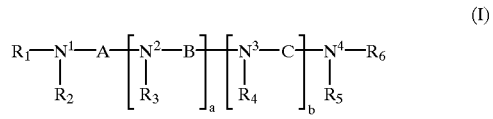

(I)

or a salt thereof with a pharmaceutically acceptable acid wherein:

$R_1$–$R_6$ may be the same or different and are alkyl, aryl, aryl alkyl, cycloalkyl, optionally having an alkyl chain interrupted by at least one etheric oxygen atom, or hydrogen;

$N^1$, $N^2$, $N^3$ and $N^4$ are nitrogen atoms capable of protonation at physiological pH's';

a and b may be the same or different and are integers from 1 to 4;

A, B and C may be the same or different and are bridging groups which effectively maintain the distance between said nitrogen atoms such that said polyamine:
(i) is capable of uptake by a target cell upon administration of said polyamine to a human or non-human animal; and
(ii) upon uptake by said target cell, competitively binds via an electrostatic interaction between the positively charged nitrogen atoms to substantially the same biological counter-anions as the intracellular natural polyamines in the target cell;

said polyamine, upon binding to said biological counter-anion in the cell, functions in a manner biologically different than said intracellular polyamines exerting an antineoplastic function, said polyamine not occurring in nature.

3. A polyamine having the formula:

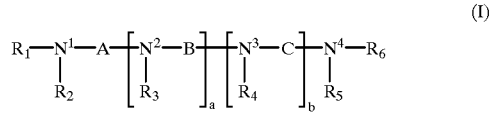

(I)

or a salt thereof with a pharmaceutically acceptable acid wherein:

17

R₁–R₆ may be the same or different and are alkyl, aryl, aryl alkyl, cycloalkyl, optionally having an alkyl chain interrupted by at least one etheric oxygen atom, or hydrogen;

$N^1$, $N^2$, $N^3$ and $N^4$ are nitrogen atoms capable of protonation at physiological pH's';

a and b may be the same or different and are integers from 1 to 4;

A, B and C may be the same or different and are bridging groups which effectively maintain the distance between said nitrogen atoms such that said polyamine:
  (i) is capable of uptake by a target cell upon administration of said polyamine to a human or non-human animal; and
  (ii) upon uptake by said target cell, competitively binds via an electrostatic interaction between the positively charged nitrogen atoms to substantially the same biological counter-anions as the intracellular natural polyamines in the target cell and are alkylene, branched alkylene, cycloalkylene, arylalkylene or a heterocyclic bridging group wherein one of said $N^1$, $N^2$, $N^3$ or $N^4$ atoms is incorporated in the ring as the hetero atom;

said polyamine, upon binding to said biological counter-anion in the cell, functions in a manner biologically different than said intracellular polyamines exerting an anti-neoplastic function, said polyamine not occurring in nature.

4. A pharmaceutical composition comprising an antineoplastic effective amount of a polyamine having the formula:

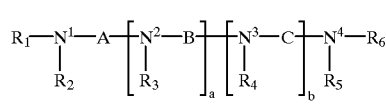

(I)

or a salt thereof with a pharmaceutically acceptable acid wherein:

R₁–R₆ may be the same or different and are alkyl, aryl, aryl alkyl, cycloalkyl, optionally having an alkyl chain interrupted by at least one etheric oxygen atom, or hydrogen;

$N^1$, $N^2$, $N^3$ and $N^4$ are nitrogen atoms capable of protonation at physiological pH's';

a and b may be the same or different and are integers from 1 to 4;

A, B and C may be the same or different and are bridging groups which effectively maintain the distance between said nitrogen atoms such that said polyamine:
  (i) is capable of uptake by a target cell upon administration of said polyamine to a human or non-human animal; and
  (ii) upon uptake by said target cell, competitively binds via an electrostatic interaction between the positively charged nitrogen atoms to substantially the same biological counter-anions as the intracellular natural polyamines in the target cell;

said polyamine, upon binding to said biological counter-anion in the cell, functions in a manner biologically different than said intracellular polyamines exerting an anti-neoplastic function, said polyamine not occurring in nature or a salt thereof with a pharmaceutically acceptable acid and a pharmaceutically acceptable carrier therefor.

5. A method of treating a human or non-human animal in need thereof comprising administering thereto an antiplastic effective amount of a polyamine having the formula:

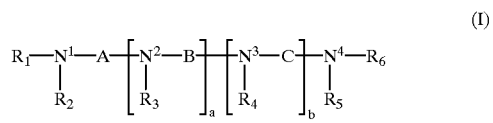

(I)

or a salt thereof with a pharmaceutically acceptable acid wherein:

R₁–R₆ may be the same or different and are alkyl, aryl, aryl alkyl, cycloalkyl, optionally having an alkyl chain interrupted by at least one etheric oxygen atom, or hydrogen;

$N^1$, $N^2$, $N^3$ and $N^4$ are nitrogen atoms capable of protonation at physiological pH's';

a and b may be the same or different and are integers from 1 to 4;

A, B and C may be the same or different and are bridging groups which effectively maintain the distance between said nitrogen atoms such that said polyamine:
  (i) is capable of uptake by a target cell upon administration of said polyamine to a human or non-human animal; and
  (ii) upon uptake by said target cell, competitively binds via an electrostatic interaction between the positively charged nitrogen atoms to substantially the same biological counter-anions as the intracellular natural polyamines in the target cell;

said polyamine, upon binding to said biological counter-anion in the cell, functions in a manner biologically different than said intracellular polyamines exerting an anti-neoplastic function, said polyamine not occurring in nature or a salt thereof with a pharmaceutically acceptable acid.

6. A polyamine having the formula:

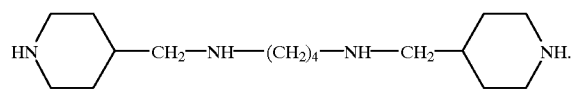

7. A polyamine having the formula:

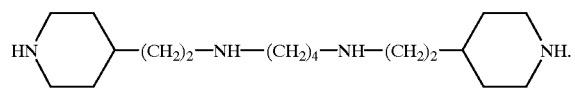

8. A polyamine having the formula:

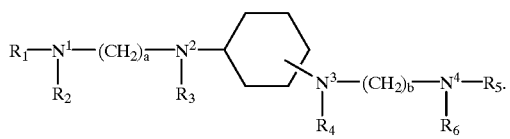

* * * * *